(12) United States Patent
Wan et al.

(10) Patent No.: US 9,696,138 B2
(45) Date of Patent: Jul. 4, 2017

(54) SIMULTANEOUS REFRACTIVE INDEX AND THICKNESS MEASUREMENTS WITH A MONOCHROMATIC LOW-COHERENCE INTERFEROMETER

(75) Inventors: Xiaoke Wan, Herndon, VA (US); Jian Ge, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 473 days.

(21) Appl. No.: 14/236,613

(22) PCT Filed: Jul. 31, 2012

(86) PCT No.: PCT/US2012/048940
§ 371 (c)(1),
(2), (4) Date: Jan. 31, 2014

(87) PCT Pub. No.: WO2013/019776
PCT Pub. Date: Feb. 7, 2013

(65) Prior Publication Data
US 2014/0168637 A1    Jun. 19, 2014

Related U.S. Application Data

(60) Provisional application No. 61/513,698, filed on Aug. 1, 2011.

(51) Int. Cl.
*G01N 21/45* (2006.01)
*G01B 11/06* (2006.01)
*G01B 9/02* (2006.01)

(52) U.S. Cl.
CPC ............ *G01B 11/06* (2013.01); *G01B 9/0207* (2013.01); *G01B 9/0209* (2013.01);
(Continued)

(58) Field of Classification Search
CPC .... G01N 21/45; G01B 11/06; G01B 11/0675; G01B 9/02022; G01B 9/0209; G01B 9/02027; G01B 9/02021; G01B 9/0207
See application file for complete search history.

(56) References Cited

U.S. PATENT DOCUMENTS 5,180,441 A    1/1993    Cornwall et al.
5,208,451 A    5/1993    Deck
(Continued)

FOREIGN PATENT DOCUMENTS

WO    WO 2004/023071    3/2004

OTHER PUBLICATIONS

International Search Report and Written Opinion for International Application No. PCT/US12/48940, dated Oct. 5, 2012.
(Continued)

*Primary Examiner* — Hwa Lee
(74) *Attorney, Agent, or Firm* — Miles & Stockbridge P.C.; David R. Schaffer

(57) ABSTRACT

A scanning monochromatic spatial low-coherent interferometer (S-LCI) can be used to simultaneously measure geometric thickness and refractive index. The probe beam of the scanning S-LCI can be an off-axis converging single wavelength laser beam, and the decomposed incident angles of the beam on the sample can be accurately defined in the Fourier domain. The angle dependent phase shift of a plane parallel plate or other sample can be obtained in a single system measurement. From the angle dependent phase shift, the geometric thickness and refractive index of the sample can be simultaneously obtained. Additionally or alternatively, the S-LCI system can interrogate the sample to profile the location and refractive index of one or more layers within the sample using the disclosed techniques.

29 Claims, 8 Drawing Sheets

(52) U.S. Cl.
CPC ..... *G01B 9/02021* (2013.01); *G01B 9/02022* (2013.01); *G01B 9/02027* (2013.01); *G01B 11/0675* (2013.01); *G01N 21/45* (2013.01)

(56) References Cited

U.S. PATENT DOCUMENTS

| | | | |
|---|---|---|---|
| 5,218,426 | A | 6/1993 | Hall et al. |
| 5,344,496 | A | 9/1994 | Stern et al. |
| 5,633,712 | A | 5/1997 | Venkatesh et al. |
| 5,642,196 | A | 6/1997 | Alves et al. |
| 5,646,734 | A | 7/1997 | Venkatesh et al. |
| 5,659,392 | A | 8/1997 | Marcus et al. |
| 6,144,449 | A | 11/2000 | Knuettel et al. |
| 6,172,752 | B1* | 1/2001 | Haruna .................. G01B 11/06 356/485 |
| 6,545,763 | B1 | 4/2003 | Kim et al. |
| 6,970,252 | B2 | 11/2005 | Knuttel |
| 7,324,210 | B2 | 1/2008 | De Groot et al. |
| 7,339,682 | B2* | 3/2008 | Aiyer .................. G01B 11/0641 356/485 |
| 7,630,071 | B2 | 12/2009 | Park et al. |
| 7,630,085 | B2 | 12/2009 | Grasser et al. |
| 7,859,682 | B2 | 12/2010 | Smith et al. |
| 8,570,524 | B2 | 10/2013 | Wan et al. |
| 8,659,845 | B2 | 2/2014 | Wan et al. |
| 2001/0046053 | A1 | 11/2001 | Hill |
| 2002/0196450 | A1* | 12/2002 | Olszak ................ G01B 11/2441 356/511 |
| 2004/0085544 | A1* | 5/2004 | De Groot ........... G01B 11/0675 356/497 |
| 2009/0319225 | A1* | 12/2009 | Mansfield .......... G01B 11/0675 702/170 |
| 2010/0188665 | A1 | 7/2010 | Dotson et al. |

OTHER PUBLICATIONS

Alexandrov et al., "Interference method for determination of the refractive index and thickness," *Optical Engineering*, Sep. 2000, 39(9): pp. 2480-2486.

Coppola et al., "Method for measuring the refractive index and the thickness of transparent plates with a lateral-shear, wavelength-scanning interferometer," *Applied Optics*, Jul. 2003, 42(19): pp. 3882-3887.

De Groot et al., "Signal modeling for low-coherence height-scanning interference microscopy," *Applied Optics*, Sep. 2004, 43(25): pp. 4821-4830.

De Groot et al., "Angle-resolved three-dimensional analysis of surface films by coherence scanning interferometry," *Optics Letters*, Jun. 2007, 32(12): pp. 1638-1640.

Fercher et al., "Optical coherence tomography—principles and applications," *Institute of Physics Publishing, Reports on Progress in Physics*, 2003, 66: pp. 239-303.

Flournoy et al., "White-Light Interferometric Thickness Gauge," *Applied Optics*, Sep. 1972, 11(9): pp. 1907-1915.

Gokhler et al., "Synthesis of a multiple-peak spatial degree of coherence for imaging through absorbing media," *Applied Optics*, May 2005, 44(15): pp. 2921-2927.

Griesmann et al., "Manufacture and Metrology of 300 mm Silicon Wafers with Ultra-Low Thickness Variations," *International Conference of Characterization and Metrology*, Mar. 2007, 931:pp. 1-6.

Griesmann et al., "Optical Flatness Metrology for 300 mm Silicon Wafers," *American Institute of Physics, Proceedings of the Conference on Characterization and Metrology for ULSI Technology*, Mar. 2005, 788: pp. 599-603.

Haruna et al., "Simultaneous measurement of the phase and group indices and the thickness of transparent plates by low-coherence interferometry," *Optics Letters*, Jun. 1998, 23(12): pp. 966-968.

Huang et al., "Optical Coherence Tomography," *Science*, Nov. 1991, 254(5035): pp. 1178-1181.

Indebetouw et al., "Imaging through scattering media with depth resolution by use of low-coherence gating in spatiotemporal digital holography," *Optics Letters*, Feb. 2000, 25(4): pp. 212-214.

National Institute of Standards and Technology (NIST), Physical Measurement Laboratory, "Wafer Flatness and Wafer Thickness Variation," [online], Jul. 1, 2012 [retrieved on Mar. 14, 2014]. Retrieved from the Internet: <URL: http://web.archive.org/web/20120701024040/http://www.nist.gov/pml/div683/grp02/wfwtv.cfm>.

Rosen et al., "Longitudinal spatial coherence applied for surface profilometry," *Applied Optics*, Aug. 2000, 39(23): pp. 4107-4111.

Tomlins et al., "Optical coherence refractometry," *Optics Letters*, Oct. 2008, 33(19): pp. 2272-2274.

Wan et al., "Accurate measurement of interferometer group delay using field-compensated scanning white light interferometer," *Applied Optics*, Oct. 2010, 49(29): pp. 5645-5653.

Wan et al., "Resolving fringe ambiguities of a wide-field Michelson interferometer using visibility measurements of a noncollimated laser beam," *Applied Optics*, Sep. 2009, 48(26): pp. 4909-4916.

Wan et al., "Scanning monochromatic spatial low-coherence interferometer," *Optics Letters*, Oct. 2011, 36(19): pp. 3807-3809.

Wang et al., "Interferometric Thickness Calibration of 300 mm Silicon Wafers," *American Society for Precision Engineering*, Summer Topical Meeting, Jul. 2005.

Wang et al., "Dual-axes confocal microscopy with post-objective scanning and low-coherence heterodyne detection," *Optics Letters*, Oct. 2003, 28(20): pp. 1915-1917.

Youngquist et al., "Optical coherence-domain reflectometry a new optical evaluation technique," *Optics Letters*, Mar. 1987, 12(3): pp. 158-160.

* cited by examiner

SIMULTANEOUS REFRACTIVE INDEX AND THICKNESS MEASUREMENTS WITH A MONOCHROMATIC LOW-COHERENCE INTERFEROMETER

CROSS-REFERENCE TO RELATED APPLICATIONS

The present application is a U.S. national stage entry of International Application No. PCT/US 12/48940, filed Jul. 31, 2012, which claims the benefit of U.S. Provisional Application No. 61/513,698, filed Aug. 1, 2011, both of which are incorporated by reference herein in their entirety.

STATEMENT REGARDING FEDERALLY SPONSORED RESEARCH

The present invention was made with U.S. government support under grant/contract no. 0705139 awarded by the National Science Foundation, Division of Astronomical Sciences, and under cooperative agreement no. W911NF-09-2-0017 awarded by the Department of Defense (DoD), Army Research Office (ARO). The U.S. government has certain rights in the invention.

FIELD

The present disclosure relates generally to systems, methods, and devices for measurement using an interferometer, and, more particularly, to simultaneous measurement of refractive index and geometric thickness of a sample using substantially monochromatic low-coherence interferometers.

BACKGROUND

The ability to accurately measure refractive index and dimensions (i.e., thickness) of a sample continues to be in high demand, especially in the areas of precision instrumentation and semiconductor fabrication. Traditionally, for general bulk optics materials, the refractometric-based techniques which measure the minimum diffraction angle of a prism are used; however, such techniques may be limited because they lack the capacity to directly measure a parallel plate sample, which is a common configuration for samples, for example, optical components and semiconductor wafers. Ellipsometers can measure the surface refractive index of a sample. However, the surface refractive index may in fact be quite different from the bulk material. In addition, ellipsometry can be relatively less precise, and ellipsometry signals may be corrupted by reflections beneath the surface.

With regard to thickness measurements, mechanical probes are common industrial tools, but they require physical contact with an object, as compared to non-invasive or non-contact optical techniques. Moreover, mechanical probes typically require access to both sides of a sample, which can be problematic for samples of relatively larger size.

Advances in the fields of optics and semiconductors present significant challenges for currently employed metrology techniques, at least with regard to accuracy and dynamic range requirements. New materials with different and varied geometric structures are emerging at a fast pace, and they often require advanced techniques to accurately determine the refractive index and geometric parameters in a non-invasive manner. Typical interferometer techniques can measure the optical length (i.e., $n*d$, where "n" represents the refractive index and "d" represents the geometric thickness) of a sample but not the refractive index or geometric thickness separately. As such, multiple techniques may be required in order to accurately extract the refractive index and the geometric thickness from the measured optical length. The increased measurement time as well as the potential for error or inaccuracy introduced by using multiple techniques presents a significant barrier to the use of high resolution interferometer measurements. For example, the National Institutes of Standards and Technology (NIST) conducted an experiment measuring the flatness and geometric thickness variation of silicon wafers. Although the optical thickness had previously been measured to nanometer resolution by a sophisticated interferometer facility, the thickness variation obtained by NIST had a much larger uncertainly of approximately 1 µm, in part because a second interferometer measuring the refractive index variation of the wafers failed to produce results with matching precision.

Shear interferometry can be used to measure thickness and refractive index of a parallel plane plate. The plate may serve as a shear interferometer, which then obtains angle dependant phase shift of a fixed laser beam transmitting through the rotating parallel plane plate. However, such techniques require the sample to be monolayer and to be accessible from both sides thereof. In addition, the measurement accuracy may be limited by the accuracy of the rotation of the sample as well as any interferometer stability issues.

A temporal low-coherence interferometer (T-LCI), or white light interferometer (WLI), is an interferometry technique that may enjoy depth resolving capability, but may lack angle resolving capability. To achieve simultaneous measurements of both refractive index and thickness of a sample, a T-LCI measures the group delay of the sample at a large number of rotation angles. T-LCI techniques thus require the sample or the light source to be rotated through a plurality of angles in order to take a measurement. For certain types of samples and/or processes, such rotation may be inadvisable or unavailable. Less precise thickness measurements can otherwise be obtained by incorporating an apparent thickness measurement taken via microscopic observation. However, such observation invariably requires at least a microscope in addition to the T-LCI system as well as additional time to make such a thickness measurement.

SUMMARY

A scanning monochromatic spatial low-coherent interferometer (S-LCI) can be used to simultaneously measure geometric thickness and refractive index. The probe beam of the scanning S-LCI can be an off-axis converging single wavelength laser beam, and the decomposed incident angles of the beam on the sample can be accurately defined in the Fourier domain. The angle dependent phase shift of a plane parallel plate or other sample can be obtained in a single system measurement. From the angle dependent phase shift, the geometric thickness and refractive index of the sample can be simultaneously obtained. Additionally or alternatively, the S-LCI system can interrogate the sample to profile the location and refractive index of one or more layers within the sample using the disclosed techniques.

In one or more embodiments, a method of determining thickness and refractive index of a sample can include directing a first beam of substantially monochromatic light onto a beam splitter at an angle so as to direct respective components of the first beam along a first optical path and along a second optical path. Light components directed along the first optical path can be incident on a reflector, while light components directed along the second optical path can be incident on the sample. The reflector can be located on an opposite side of the beam splitter from the sample.

The method can further include combining light components from the first optical path reflected by the reflector with light components from the second optical path reflected by the sample so as to generate an interference pattern. In addition, the method can include changing a distance between the sample and the beam splitter. The directing and the combining can be repeated to generate another interference pattern. The method can also include determining the thickness and refractive index of at least a portion of the sample on the basis of the generated interference patterns.

In one or more embodiments, a method of determining thickness and refractive index of a sample can include providing a spatial low-coherence interferometer with the sample in one of the interferometer pathways. The interferometer can be interrogated using a first light beam from a substantially monochromatic light source. The light beam can be directed at an angle with respect to the interferometer. The method can further include translating one of the sample and the interferometer with respect to the other so as to produce a plurality of interferograms from light reflected from interfaces of the sample. Thickness and refractive index information for at least a portion of the sample can be determined based on the plurality of interferograms.

In one or more embodiments, a system for determining thickness and refractive index information for a sample can include a substantially monochromatic light source, an interferometer, first and second optical components, first and second detectors, a scanning mechanism, and a processor. The interferometer can form two beam paths. The sample can be arranged with respect to one of the beam paths. The first optical components can be constructed and arranged to generate a first light beam from an output of the light source. The first light beam can be directed at an angle with respect to an axis of the interferometer. The second optical components can be constructed and arranged to generate a collimated light beam from the output of the light source. The collimated light beam can be directed to the interferometer along the axis. The first detector can be arranged to detect light output from the interferometer at an angle with respect to the interferometer axis, while the second detector can be aligned with the interferometer axis to detect light reflected along the axis. The scanning mechanism can be configured to move one of the sample and the interferometer with respect to the other in a direction parallel to the interferometer axis. The processor can be configured to use signals from the first and second detectors to determine thickness and refractive index information for at least a portion of the sample.

In one or more embodiments, a sample measurement method can include directing a first portion of substantially monochromatic light to a first arm of an interferometer. The first arm can have a reflection surface arranged at a first distance along an input beam path of the first arm. The reflection surface can reflect light incident thereon from said first arm input path to an output beam path. The method can further include directing a second portion of the substantially monochromatic light to a second arm of the interferometer. The second arm can have a sample arranged along the input beam path of the second arm. Internal boundaries or external surfaces of the sample can reflect light incident thereon from said second arm input path to the output beam path. The method can also include translating the sample while directing the first and second portions of the light. An interference pattern can be formed by the combination of light in the output beam path when one of said internal boundaries or externals surfaces of the sample is at a distance along the second arm input beam path approximately equal to the first distance along the first arm input beam path. The combination of light can be detected, and signals indicative of a plurality of the interference patterns formed during the translating can be generated. The method can further include calculating at least a refractive index and a thickness of the sample based on the signals.

In one or more embodiments, a sample measurement method can include, using a spatial low-coherence interferometer, illuminating a sample with substantially monochromatic light while translating the sample in a thickness direction thereof to generate a plurality of interferograms. The method further includes calculating refractive index and thickness of the sample based on the plurality of interferograms. The calculating can include generating Fourier phase data by subjecting the plurality of interferograms to a Fourier transform.

In one or more embodiments, a system for measuring a sample can include a light source, an interferometer, a translation device, a detection device, and a controller. The light source can produce a narrow band of light at a substantially single wavelength. The interferometer can have a reference beam path, a sample beam path, and a beam splitter. The beam splitter can divide light input to the interferometer and direct first and second portions of the light to the reference beam path and the sample beam path, respectively. The first portion of the light can be incident on a reference mirror in the reference beam path while the second portion of the light can be incident on the sample in the sample beam path at an angle with respect to a thickness direction of the sample. The light reflected by both the reference mirror and the sample can be combined as an output of the interferometer. The translation device can translate one of the interferometer and the sample with respect to the other in a thickness direction of the sample. The detection device can detect the interferometer output and can generate interferogram signals based thereon. The controller can be coupled to the detector and can simultaneously determine refractive index and geometric thickness of at least a portion of the sample based on the generated interferogram signals. The controller can be configured to perform a Fourier transform on at least two of the interferogram signals so as to generate Fourier phase data, to calculate phase delay caused by the sample based on the phase data from the at least two of the interferogram signals, and to calculate the refractive index and the thickness of the at least a portion of the sample based on the calculated phase delay.

In one or more embodiments, a system for measuring a sample can include a spatial low-coherence interferometer, a translation device, and a controller. The spatial low-coherence interferometer can have a monochromatic light input and can output combined light reflected by a sample in a sample path and by a reference mirror in a reference path. The translation device can move one of the sample or the interferometer with respect to the other in a thickness direction of the sample. The controller can calculate refractive index and thickness of the sample based on interferograms detected in light output from the interferometer with the sample at different locations in the thickness direction.

Objects and advantages of embodiments of the disclosed subject matter will become apparent from the following description when considered in conjunction with the accompanying drawings.

BRIEF DESCRIPTION OF DRAWINGS

Embodiments will hereinafter be described with reference to the accompanying drawings. Except where explicitly noted, the figures have not been drawn to scale. Where applicable, some features have not been illustrated to assist in the illustration and description of underlying features. Throughout the figures, like reference numerals denote like elements.

DETAILED DESCRIPTION

Figure 1:
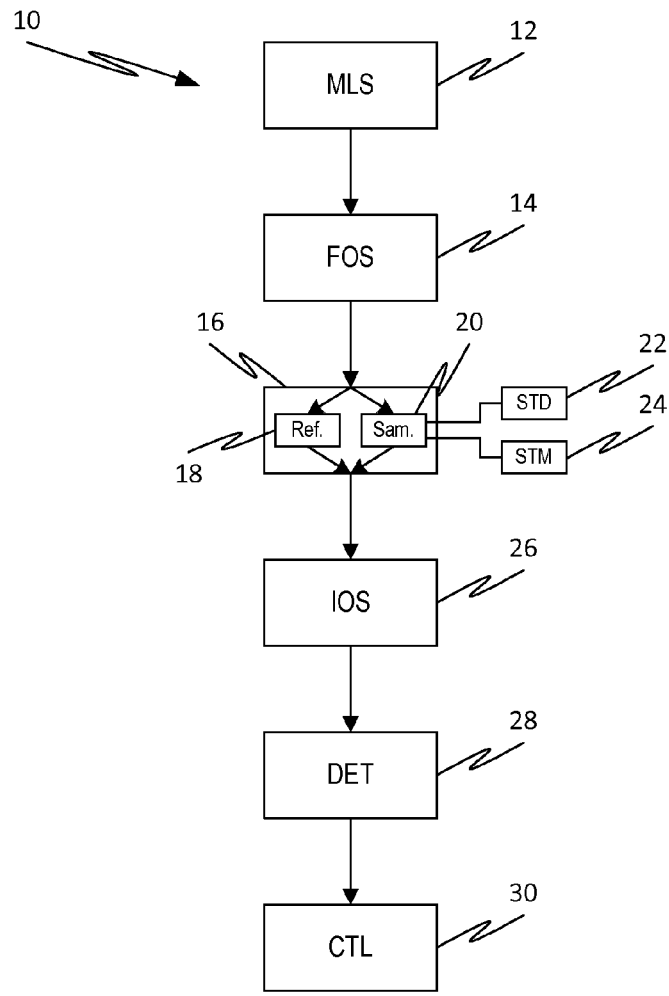
FIG. 1 is a general schematic diagram of aspects of a scanning spatial low-coherence interferometer (S-LCI) system for simultaneously measuring refractive index and geometric thickness of a sample, according to one or more embodiments of the disclosed subject matter.

A simplified interferometer layout can include a two beam interference structure with a substantially single wavelength (monochromatic) laser source. The interference contrast or visibility can be nearly constant along the overlapped beam path (i.e., at the output of the interference structure), which may make such a configuration less desirable for 3-D profiling or tomography. In such applications, a low-coherence interferometer may be desirable to take advantage of depth discrimination capability. A low-coherence interferometer (LCI) can employ a white light interferometer (WLI) when using a broadband light source. Because of temporal coherence gating mechanism employed in such systems, it may also be referred to as a temporal low-coherence interferometer (T-LCI).

In contrast, disclosed herein is a spatial coherence gating mechanism in a spatial low-coherence interferometer (S-LCI). In particular, a novel implementation of a scanning S-LCI is disclosed herein, which retains similar data acquisition and processing to scanning T-LCI. The probe beam and detecting schemes of the disclosed S-LCI can be arranged in off-axis configurations (i.e., angled with respect to a surface normal of the sample). In addition, the use of S-LCI allows for the combination of depth resolving and angle resolving capabilities, which may not be achievable with conventional T-LCI systems. For example, as disclosed herein, the S-LCI can provide angle dependant phase measurements at multi-interface depths of a sample (e.g., a glass plate), which can then be used to simultaneously determine the bulk refractive index and the geometric thickness of the sample. Embodiments of the disclosed subject matter therefore find application in high precision metrology as well as other contemplated applications.

Embodiments of the disclosed S-LCI system can measure the angle dependant phase shift of a parallel plane plate at a single wavelength (i.e., substantially monochromatic). The measured phase shifts can then be used to simultaneously determine the refractive index and geometric thickness of the sample using a single instrument. While such simultaneous measurements of thickness and refractive index of a homogenous parallel plane plate are possible using shear interferometer configuration, such a configuration requires measurement of the angle dependent phase shift of a fixed laser beam transmitted through the sample as it is rotated. In contrast, embodiments of the disclosed S-LCI system can be potentially more useful than a shear interferometer based on its ability to probe samples from the front (i.e., front probing) rather than requiring transmission through the sample. The front-probing configuration allows the interrogation of embedded samples or relatively large size samples. In addition, embodiments of the disclosed S-LCI system may enjoy the capability of providing layer-by-layer measurements for a multi-layer structure.

T-LCI systems may be capable of depth resolving measurements, but, in contrast to the disclosed S-LCI systems, they lack angle resolving capability. Thus, to achieve simultaneous measurements of both refractive index and thickness, it would be necessary for a T-LCI system to measure the group delay of a sample at a large number of rotation angles. Alternatively, a compromise may be reached with respect to precision and working distance of the T-LCI system by incorporating an apparent thickness measurement made by a microscope.

In contrast, embodiments of the disclosed S-LCI systems may enjoy both depth resolving and angle resolving capability. Moreover, the usage of single wavelength laser source in embodiments of the disclosed S-LCI systems provides additional advantages over T-LCI system, including, but not limited to, high optical intensity, wide selection in wavelengths, convenience in amplitude modulation and wavelength manipulation, and freedom from chromatic dispersion (e.g., by raster scanning using acousto-optic deflectors). The spatial "bandwidth" of the laser source can also be manipulated by adjusting the incident angle or the beam numerical aperture (NA).

While the disclosed S-LCI system may share similarities with T-LCI and/or WLI systems, for example, interference signal formation or data processing, the S-LCI system differs in several significant respects. For example, the light source of the S-LCI system is a converging single wavelength (substantially monochromatic) laser beam at relatively large incident angle (i.e., approximately 30°) with the beam angular intensity distribution equivalent to the spectral distribution of the white light source in a T-LCI. While T-LCI systems also measure samples non-invasively (such that samples may be reused or retained), the S-LCI systems disclosed herein do not require any angular rotation or spatial recordation of angles, for example, with a detector array. Rather, the angle can be defined in the frequency domain with a high degree of accuracy.

In addition, in embodiments of the disclosed subject matter, the S-LCI system can include an on-axis monitoring channel, which normally is more accurate than other scanning distance monitoring techniques such as the use of motor position readings. The on-axis monitoring channel may also be used to account for instabilities in the reference arm of the interferometer.

A simplified schematic diagram of components of an S-LCI system 10 is shown in FIG. 1. The S-LCI system can include a substantially monochromatic light source (MLS) 12, for example a single wavelength laser. Light from the MLS 12 can be provided to a focusing optical system (FOS) 14, which can form the monochromatic light into a converging beam. The converging beam can be incident on interferometer 16, which separates and directs the input converging beam (e.g., via a beam splitter) into a reference arm 18 portion and an interrogation arm 20 portion containing a sample therein. A sample translation device (STD) 22 can move the sample within the interrogation arm 20 such that different portions of the sample are at a reflection location in the interrogation arm 20. A sample tracking module (STM) 24 can monitor displacement of the sample by the STD 22, for example by using on-axis interference fringe counting.

Light from both the reference arm 18 and the interrogation arm 20 are recombined by the interferometer 16 and directed to an interference optical system (IOS) 26. The IOS 26 can focus the light from the interferometer 16 onto a detector (DET) 28, which generates signals based on the intensity of light detected. The signals are supplied to controller (CTL) 30, which extracts interferogram signals therefrom. Together with information from STM 24 regarding displacement of the sample, CTL 30 uses the interferogram signals to simultaneously synthesize thickness and refractive index information for the sample.

Figure 2B:
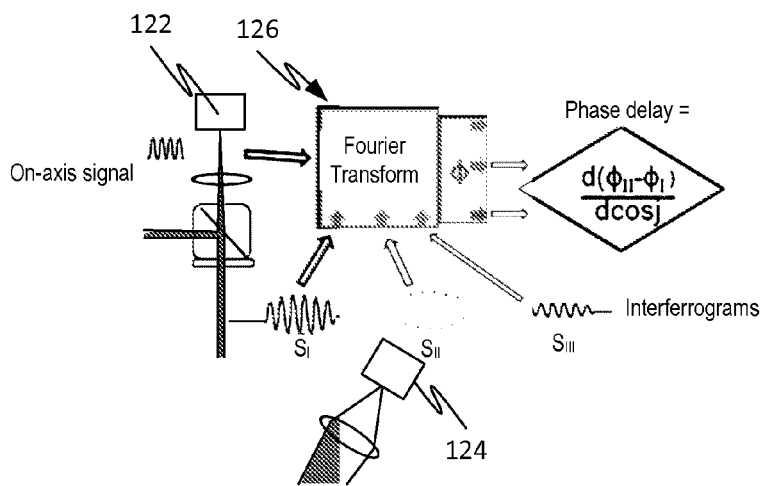
FIG. 2B is an annotated diagram of detectors and a processor for an S-LCI system illustrating interferogram inputs and phase delay output, according to one or more embodiments of the disclosed subject matter.
Figure 2A:
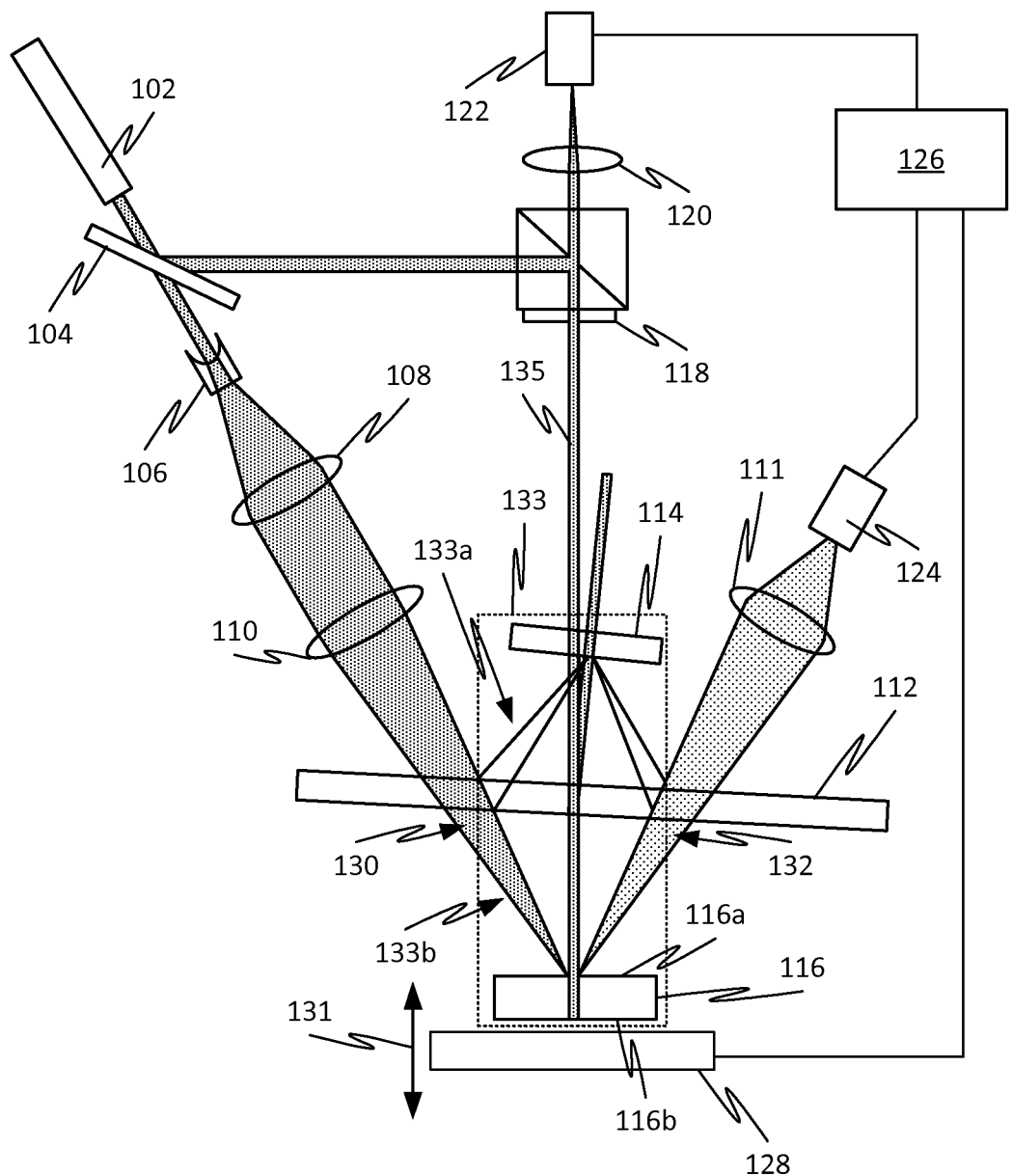
FIG. 2A is a schematic diagram showing arrangement of components of an S-LCI system, according to one or more embodiments of the disclosed subject matter.

Referring now to FIG. 2A, a more detailed schematic diagram of an S-LCI system according to an embodiment of the disclosed subject matter is shown. The scanning S-LCI can be used to measure the bulk refractive index and the geometric thickness of a sample 116, for example, a glass plate, having a front surface 116a and a back surface 116b. The interferometer 133 includes a beam splitter 112 (e.g., a 50/50 beam splitter with a dielectric coated surface, which may be the surface closest to the sample 116) and a fixed reflector 114 (e.g., a wedged, uncoated BK7 plate providing front surface reflection in the fixed interferometer arm 133a). The sample 116 is placed in the scanning arm 133b of the interferometer 133. A translation stage 128 may be provided for moving the sample 116 in a thickness direction 131 to provide multi-surface reflections to the scanning arm 133b. Additionally or alternatively, the translation stage may provide 2-D or 3-D motion so as to scan different parts of the sample. The translation stage can be, for example, a stepper motor. However, any type of translation device may be used, including devices that may allow faster and/or more precise scanning than a stepper motor. Optionally, when changing the distance between the sample 116 and beam splitter 112, the distance between the beam splitter 112 and the reflector 114 is maintained. Scanning of the sample or of the optical system in the thickness direction may be at such translation and detection speeds to enable a full scan of the sample thickness in, for example, less than a second.

For example, the sample may be an uncoated parallel plane BK7 glass plate; however, applications of the disclosed embodiments are not limited to glass plate or even completely transparent samples. Instead, embodiments of the disclosed subject matter are applicable to a wide range of samples. For example, appropriate selection of the interrogating light (e.g., visible or invisible substantially monochromatic electromagnetic radiation) can allow for measurement of layers or internal defects in a semiconductor sample.

The light source 102 can be a substantially monochromatic light source, for example, a wavelength-stabilized He—Ne laser at 632.8 nm with a state of polarization in the S-plane. Light from the source 102 can be divided into two beams by splitter 104. A first beam 130 (i.e., the probe beam) can be formed as a converging beam, which enters the interferometer at an angle j (see FIGS. 3A-3C) of approximately 30° (e.g., approximately 32° from the normal to the sample surface 116a). For example, the probe beam 130 may form a spot size on the sample 116 on the order of 1 μm, although smaller or larger spots sizes are also possible depending on the selection of the wavelength of the light source. For example, use of the light in the ultra-violet range can allow sub-micron spot sizes.

The second beam 135 (i.e., the on-axis beam) from the splitter 104 can be formed as collimated beam and directed on-axis (i.e., substantially parallel to the normal to the sample surface 116a) with respect to the interferometer using splitter 118. Reflections of the on-axis beam 135 from the interferometer 133 and the sample 116 can be aligned back towards the laser source direction with a negligible off-axis cosine error, for example, less than $1 \times 10^{-7}$. An optical isolator associated with splitter 118 can block any optical feedback to the laser cavity. In addition, the on-axis signal may be conveyed to a first detector 122 (e.g., an AC-coupled photodetector) by way of one or more lenses 120. The on-axis interference signal detected by the first detector 122 can treat the multi-surface reflectors of the sample 116 as a single reflector thereby allowing the signal to be used for monitoring the actual scanning distance of sample 116.

However, other methodologies for monitoring the scanning distance of the sample in an accurate manner, in place of or in addition to the on-axis interference signal, are also possible according to one or more contemplated embodiments. For example, an independent optical system could separately interrogate the sample at a location coincident with or remote from the probe beam to measure displacement during scanning. In another example, a surface portion of the sample coincident with or remote from the probe beam could be used as a mirror of a Fabry-Perot etalon, whereby changes in the resonant frequency of the etalon provides an indication of the translation of the sample. In still another example, acoustic or electromagnetic wave transceivers could be used to detect an amount of displacement based on reflected waves from the sample. In yet another example, a high-precision translation stage incorporating a micro-encoder could be used to monitor displacement.

The converging beam 130 can be formed by expanding the laser beam using beam expander 106 and then focusing one or more lenses 108, 110. Alternatively, beam 130 may be a diverging or uncollimated beam. The converging beam 130 can be directed at approximately the front surface 116a of the sample 116 at a location that substantially overlaps (or is proximal to) the on-axis beam near the sample surface. Alternatively, the converging beam 130 can be focused at approximately the surface of the reference reflector 114 and the focal spot can overlap with (or at least be proximal to) the location of the on-axis beam 135 at the reference reflector 114. A second detector 124 (e.g., another AC-coupled photodetector having an active area of approximately 1 mm×1 mm) can collect the off-axis reflections 132 behind one or more imaging lenses 111.

Figure 3A:
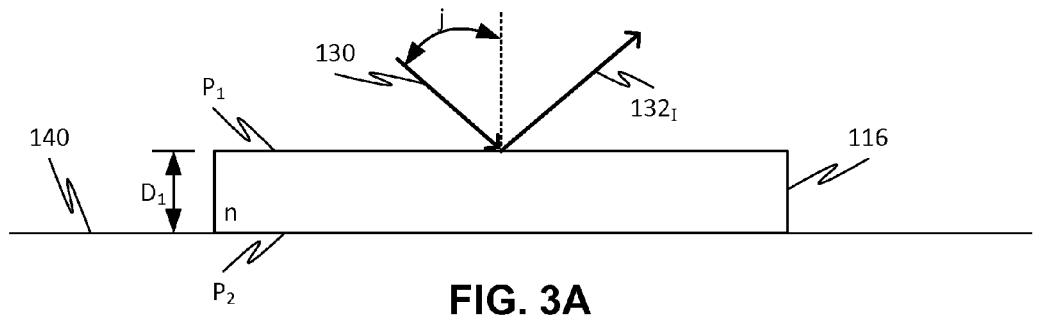
FIGS. 3A-3C are simplified elevation views of the interaction of the probe beam with surfaces of the sample to produce reflected beams as the sample is translated in a thickness direction, according to one or more embodiments of the disclosed subject matter.

As the sample 116 is moved toward the beam splitter 112 (from a location substantially remote from the beam splitter) in a thickness direction of the sample, probe beam 130 is reflected from the front surface $P_1$ (e.g., surface 116a in FIG. 2A) of the sample 116 to generate reflected beam $132_I$, as shown in FIG. 3A. However, no interference signal is detected by detector 124 due to the low coherence nature of the light until the front surface $P_1$ is at a same apparent distance from the beam splitter 112 as the fixed reflector 114. With the sample at this first location, a first low-coherence signal, $S_I$, is detected by the detector 124. For example, the surface $P_1$ may be at a distance $D_1$ from a reference plane 140 when the interference signal is detected by the detector 124. For example, the reference plane 140 may coincide with a location of the back surface $P_2$ (e.g., surface 116b in FIG. 2A) of the sample 116 when the interference signal is detected; however, the reference plane 140 is not required to be at such a location and other locations for the reference plane 140 are also possible.

Figure 3B:
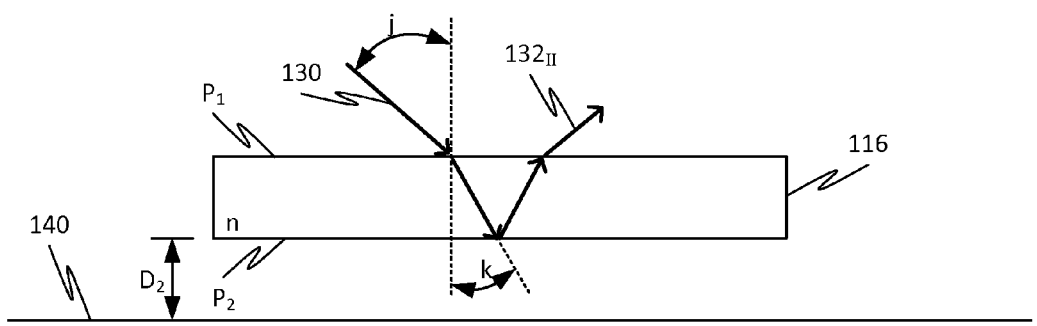

As the sample 116 moves from the first location and toward the beam splitter 112, the interference signal strength detected by detector 124 may decay until a second location is reached. At the second location, the back surface $P_2$ of the sample is at a same apparent distance from the beam splitter 112 as the fixed reflector 114. As shown in FIG. 3B, at this second location, the back surface 116b ($P_2$) of the sample reflects the probe beam 130, which travels through the thickness of the sample 116, to generate reflected beam $132_{II}$. The combination of the reflected beam $132_{II}$ with the reference beam from the fixed reflector 114 results in a second interferogram signal, $S_{II}$, at the detector 124. For example, the second location may be at a distance D2 from the reference plane 140 with $D_2$ being greater than $D_1$.

Figure 3C:
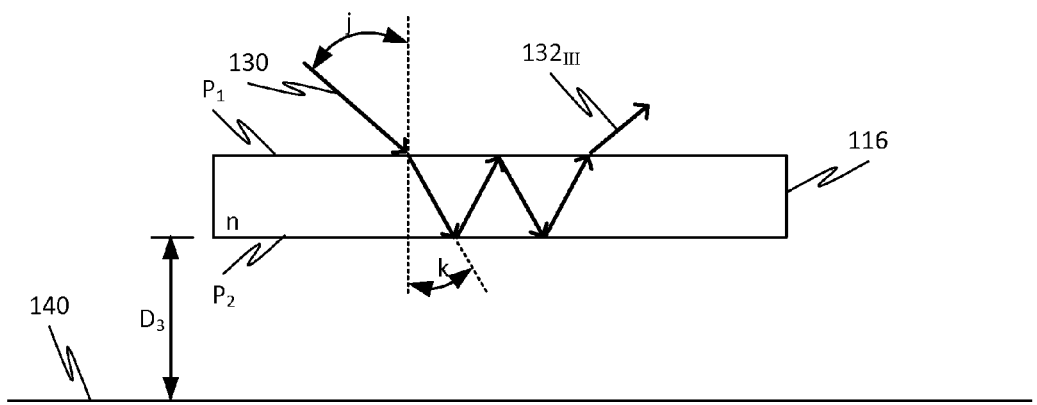

As the sample 116 moves from the second location and toward the beam splitter 112 in a thickness direction of the sample (i.e., in a direction normal to the surface of the sample), the interference strength detected by detector 124 may decay until a third location is reached. At this third location, multiple reflections between the front surface $P_1$ and the back surface $P_2$ within the sample 116 may result in an apparent distance for the sample from the beam splitter 112 that is the same as the fixed reflector 114. As shown in FIG. 3C, at this third location, the probe beam 130 is initially reflected by the back surface $P_2$, then reflected back into the interior of the sample by the front surface $P_1$, then reflected a second time by the back surface $P_2$ before forming reflected beam $132_{III}$ emanating from the sample 116. The combination of the reflected beam $132_{III}$ with the reference beam from the fixed reflector results in a third interferogram signal, $S_{III}$, at the detector 124. This third signal, $S_{III}$, may be substantially weaker than either $S_I$ or $S_{II}$ due to the multiple surface reflections within the sample. For example, the third location may be at a distance $D_3$ from the reference plane 140 which is greater than both $D_1$ and $D_2$.

Referring to FIGS. 2A-2B, a controller (or processor) 126 can be provided to control one or more component of the S-LCI system. For example, controller 126 can be operatively coupled to detector 124 and can receive interferogram signals therefrom, for example, signals $S_I$-$S_{III}$. Controller 126 can be configured to determine Fourier amplitude and/or Fourier phase data by subjecting the interferogram signals to a Fourier transform, as described in more detail below. In addition, controller 126 can be operatively coupled to detector 122 and can receive an on-axis interference signal therefrom. Controller 126 can be configured to measure displacement of sample 116 in the thickness direction 131 and can use the measurements in the determination of refractive index and/or geometric thickness of the sample 116. Additionally or alternatively, controller 126 can be operatively coupled to translation stage 128 for controlling the motion thereof.

Figure 4:
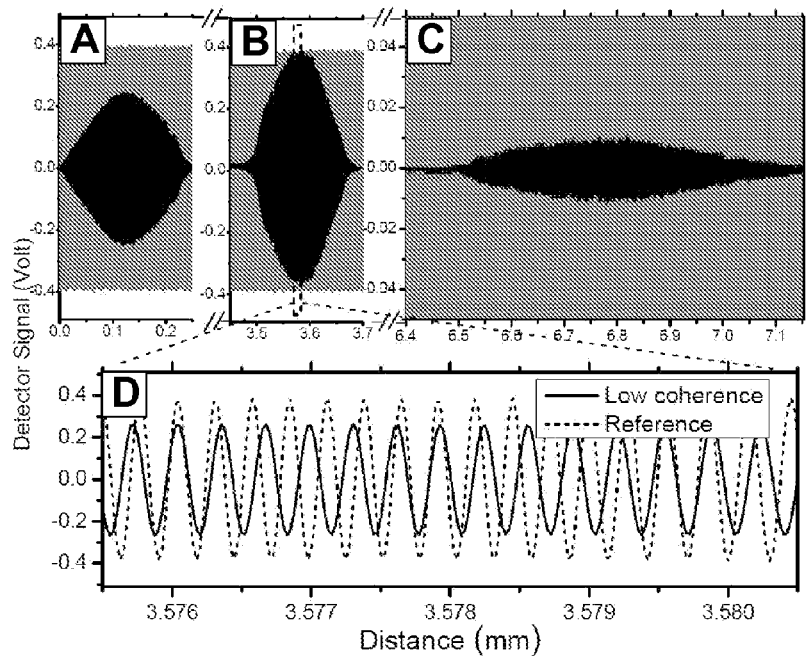
FIG. 4 shows multiple graphs (panels (A)-(D)) of low-coherence and reference signals over a long scan of approximately 25000 (on-axis) fringes for a glass plate sample. The lower panel (D) shows a close-up view of a portion of the graph of panel (B).

Panels (A)-(C) in FIG. 4 show the simultaneously acquired on-axis pseudo-sinusoidal signal together with the first three low-coherence interferogram signals, respectively. Panel (D) in FIG. 4 shows a close-up view of the detailed signal waveforms from panel (B) in FIG. 4. In particular, panels (A)-(C) show three-cleaved windows of low-coherence signals and reference signal (i.e., the on-axis interference signal) over a long scan of approximately 25000 (on-axis) fringes. The vertical scale in panel (C) is different from that in panels (A)-(B) by about a factor of 10. As is evident from panel (D) in FIG. 4, the off-axis signal oscillates at a lower rate than the on-axis signal, due at least in part to the off-axis reflected beam from the translating sample experiencing a lower Doppler shift than the on-axis beam.

The wide envelopes of the low-coherence signals are due, at least in part, to spherical aberration, which is equivalent to the chromatic dispersion in a T-LCI signal. The signal envelops can be compressed by applying analog or numerical compensation schemes, for example, by employing compensation schemes similar to the chromatic dispersion compensation schemes employed in T-LCI signal processing. Since the low-coherence signals may be clearly separated, special effort may not necessarily be required to compensate for any spherical aberration effect, although various schemes or efforts can be used to compensate for spherical aberration as needed. In fact, the stretched signal envelops may put a lower demand on the dynamic range of the signal detecting hardware.

If x represents the common air thickness difference between the two arms 133a, 133b of the interferometer (with the sample at the first through third locations where interferograms are detected), the angle dependant phase delays of the interferogram signals can be expressed as:

$$\phi^{SI}(x, \cos j) = \frac{4\pi}{\lambda}(n_{air}x * \cos j + n_1 t_1 * \cos q), \tag{1a}$$

$$\phi^{SII}(x, \cos j) = \frac{4\pi}{\lambda}(n_{air}x * \cos j + n_1 t_1 * \cos q - n_2 t_2 * \cos k) \pm \pi, \tag{1b}$$

$$\phi^{SIII}(x, \cos j) = \frac{4\pi}{\lambda}(n_{air}x * \cos j + n_1 t_1 * \cos q - 2n_2 t_2 * \cos k) \pm \pi, \tag{1c}$$

where $\lambda$ is the wavelength of the laser beam in vacuum; $n_{1,2}$ represents the refractive index of the beam splitter 112 and the sample 116, respectively; $t_{1,2}$ represents the thickness of the beam splitter 112 and the sample 116, respectively; and j, q, k represents the incident angle in the air, in the beam splitter 112, and in the sample 116, respectively.

In the S-LCI system, cos j is equivalent to the optical frequency. The complex inverse Fourier transform of the lth clipped interferogram signal, $S_l(x)$, produces the angular spectrum and the local phase delay:

$$G_l(\cos j)\exp(i\phi^{Sl}(d_l, \cos j)) = \int_{d_l - W_l}^{d_l + W_l} S_l(x) e^{i\frac{4\pi}{\lambda}\cos j*(d_l - x)} dx, \tag{2}$$

where $d_l$ is an arbitrarily chosen air thickness value near the center region of the interferogram signals, and the integral range $W_l$ is chosen to overlap the entire range of each interferogram signal window. The integral can be accurately computed as a summation over equal on-axis phase steps, as the phase shift of the pseudo-sinusoidal on-axis signal is determined as a function of the scanning air thickness using a fast Hilbert transform algorithm.

Figure 5A:
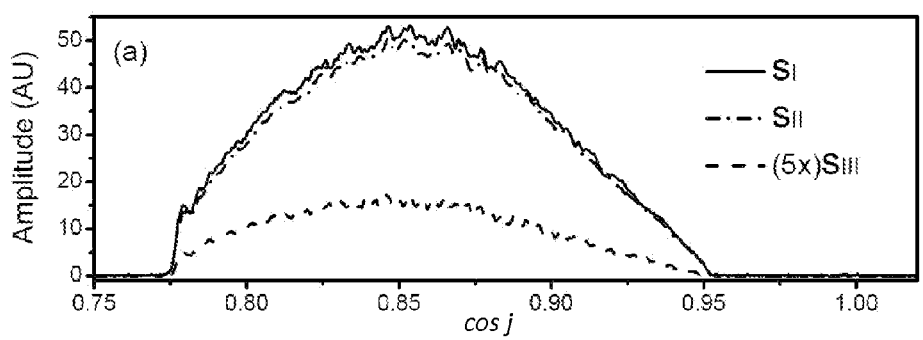
FIGS. 5A-B are graphs of Fourier amplitude and unfolded Fourier phase of low-coherence signals calculated for the glass plate sample.
Figure 5B:
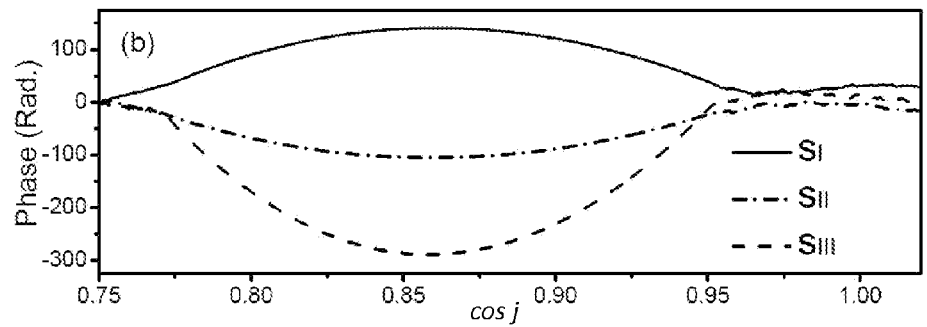

FIGS. 5A-5B show the Fourier amplitude (FIG. 5A) and the unfolded Fourier phase (FIG. 5B) of the interferogram (low-coherence) signals. The unit cosine value, or unit "frequency," corresponds to the on-axis reference signal. The amplitude of the $S_{III}$ signal in FIG. 5A has been multiplied by a factor of five so as to be visible on the sample scale as the other signals in the figure.

The Fourier amplitude largely represents the intensity distribution profile of the converging beam, which includes some irregular signatures as clearly illustrated from the $S_I$ and $S_{II}$ curves in FIG. 5A. The Fourier phase represents the phase dispersion of the interferogram signal. The angle dependant surface reflection and transmission can be determined from the Fourier amplitudes. According to Fresnel's equations, a coarse measurement of the refractive index can be obtained to an accuracy of approximately 0.003. Careful control of the state of polarization of the input beam can further improve the accuracy with which the refractive index is determined.

The phase delay of the sample 116 can be precisely determined from the phase shift between any two interferogram signals, for example, from the first two S-LCI signals by applying Eqs. (1a)-(1b):

$$\frac{4\pi}{\lambda} n_2 t_2 * \cos k = \tag{3}$$

$$\phi^{SI}(d_I, \cos j) - \phi^{SII}(d_{II}, \cos j) + (\phi^{ref}(d_{II}) - \phi^{ref}(d_I)) * \cos j \pm \pi,$$

where $\phi^{ref}$ represents the phase shift of the on-axis signal. Combining with Snell's law:

$$n_2 \sin k = n_{air} \sin j, \tag{4}$$

a least-squares fit to the data can produce a set of results, Set(I-II), for the relative refractive index $n_2/n_{air}$, the thickness $t_2$, the phase delay at normal incidence $n_2 t_2$ and the apparent thickness $t_2 n_{air}/n_2$. The combination of precise local phase determinations and the long range continuous fringe counting from the front to the back surfaces can produce high precision measurements. In addition, the measurement can be immune to instability of the fixed arm of the interferometer, as the scanning distance x in eqs. (1) and (2) already includes the instantaneous separation change between the reference plate and the beam splitter as a contribution to the distance scanning. The fluctuation of the refractive index of the air medium does not affect the phase delay measurement.

In an example of the disclosed embodiments of the S-LCI system, refractive index and thickness of a sample glass plate were measured using the setup of FIG. 2A. The data processing of 30 consecutive scans in 15 round-trips determined the relative refractive index and the thickness of the plate as $1.51531 \pm 2.1 \times 10^{-5}$ and $5.3455$ mm$\pm 85$ nm respectively by using the first ($S_I$) and the second ($S_{II}$) interferogram signals. A single scan is sufficient to determine the refractive index and thickness details of the sample. However, multiple scans can be used to study the repeatability of the measurement system.

Additional results are listed in Table 1, which includes the commercial nominal values and the index values determined from the Fourier amplitudes. As is apparent, the results using the disclosed S-LCI techniques and systems are consistent and agree well with commercial nominal values. Differences between the sets of results can be explained as an effect of sample rotation during translation. Since the translation path is highly repeatable, such systematic errors can be calibrated and/or accounted for to further improve the absolute accuracy of the system.

TABLE 1

Refractive Index and Thickness of BK7 Glass Plate.
Commercial and S-LCI determined values.

| | Refractive index | Thickness | Phase delay (rad.) | Apparent Thickness |
|---|---|---|---|---|
| Set (I-II) | 1.51531 ± 2.1 × 10⁻⁵ | 5.3455 mm ± 85 nm | 160806.2 ± 4.9 | 3.527657 mm ± 7 nm |
| Set (II-III) | 1.515442 ± | 5.3458 nm ± | 160822.4 ± | 3.527730 mm ± |

TABLE 1-continued

Refractive Index and Thickness of BK7 Glass Plate.
Commercial and S-LCI determined values.

| | Refractive index | Thickness | Phase delay (rad.) | Apparent Thickness |
|---|---|---|---|---|
| | 7.4 × 10$^{-5}$ | 160 nm | 8.9 | 11 nm |
| Set(I-III) | 1.51537 ± 2.0 × 10$^{-5}$ | 5.3457 mm ± 80 nm | 160814.7 ± 4.5 | 3.527694 mm ± 5 nm |
| Within typical fringe | 1.5152955 ± 4.0 × 10$^{-7}$ | 5.34543 mm ± 1.3 nm | 160802.4535 ± 4.5 × 10$^{-3}$ | |
| Commercial value | 1.51509 ± 5 × 10$^{-4}$ | 5.346 mm ± 5 μm | | |

Embodiments of the disclosed S-LCI systems can find application in a variety of fields, including, but not limited to, metrology, diagnosis of internal defects and artifacts in a low scattering medium, 3-D surface profiling, examination of thin-film layers, and diffraction tomography. In addition, embodiments of the disclosed S-LCI systems may be combined with existing or later-developed T-LCI systems, confocal microscopy, and/or ellipsometry systems to create new and useful tools and functions.

Embodiments of the disclosed S-LCI systems are not limited to the specific optical components and arrangements illustrated in FIG. 2A. Rather, various optical components and arrangements can be used to obtain the same or substantially similar optical performance, according to one or more contemplated embodiments. In addition, although the sample 116 is discussed as being translated with respect to the beam splitter 112, it is also possible for the optical system (or components thereof) to be translated with respect to the sample, which remains fixed.

Figure 6:
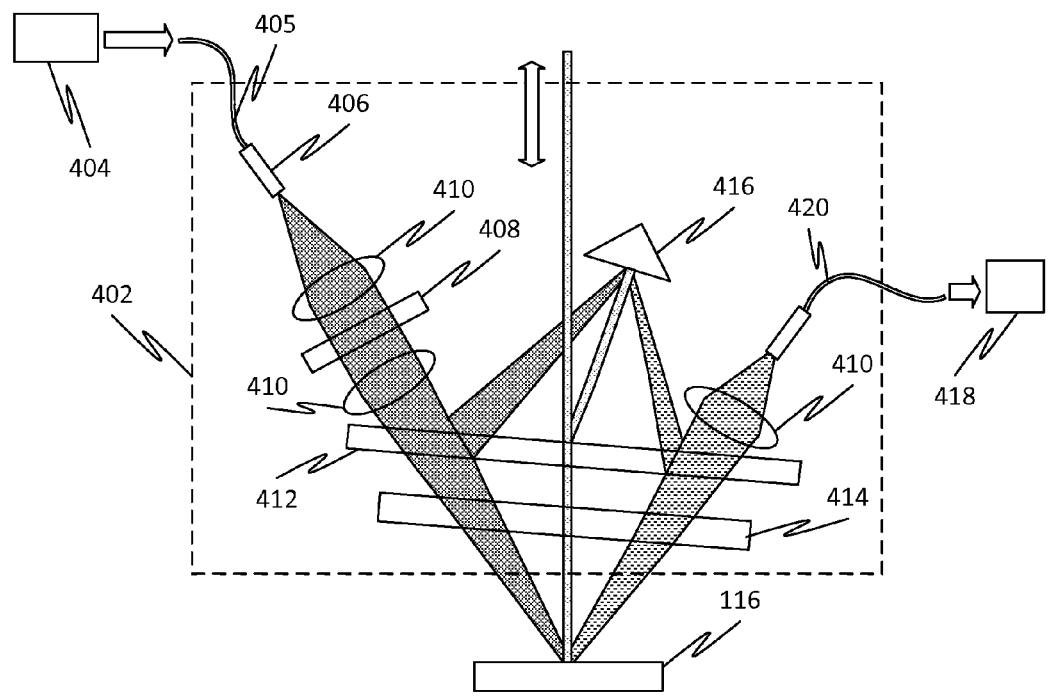
FIG. 6 is a schematic diagram showing a configuration for an S-LCI system with a fixed sample and movable optical system, according to one or more embodiments of the disclosed subject matter.
Figure 7:
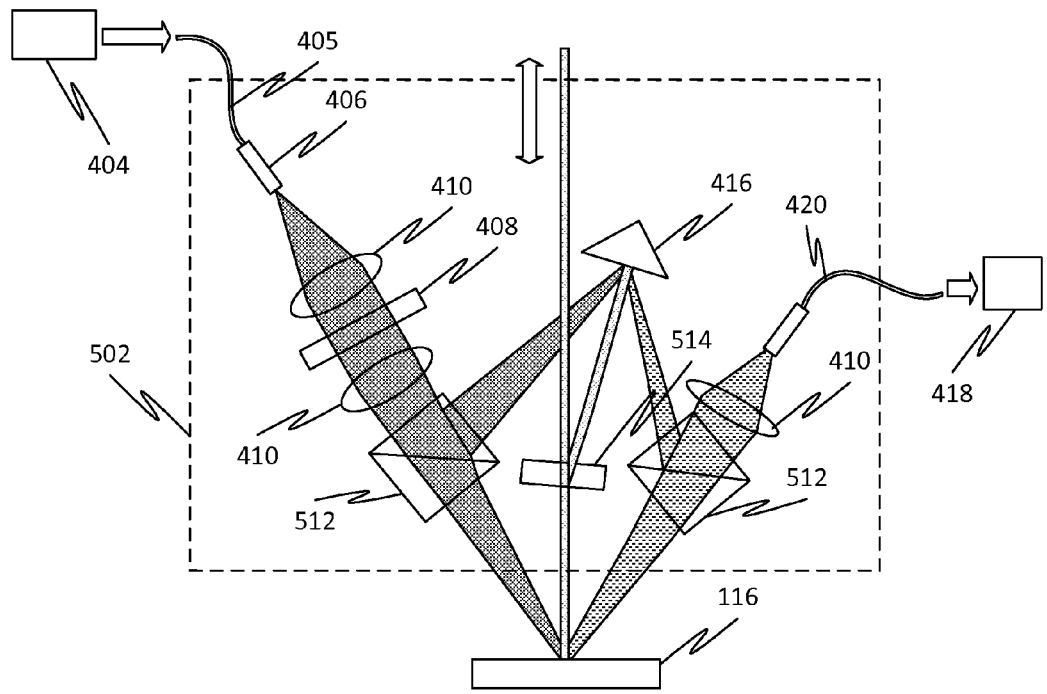
FIG. 7 is a schematic diagram showing a configuration for an S-LCI system with multiple beam splitters, according to one or more embodiments of the disclosed subject matter.
Figure 8:
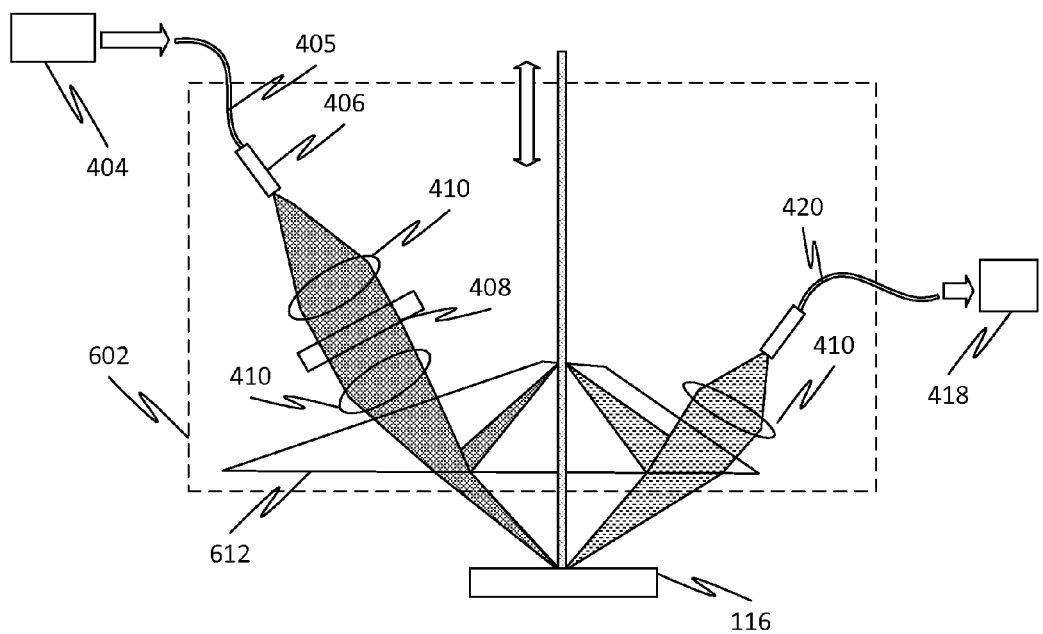
FIG. 8 is a schematic diagram showing a configuration for an S-LCI system with a prism, according to one or more embodiments of the disclosed subject matter.

FIGS. 6-8 show various configurations for an S-LCI system according to the teachings of the disclosed subject matter. For example, FIG. 6 shows a configuration of an S-LCI system for moving various optical components with respect to the sample 116, while maintaining the sample 116 in a fixed position. Optical components 402 can be located, for example, on a translation platform (not shown), which allows movement of the optical components 402 toward or away from the sample 116. The various optical components 402 can be locked in position with respect to each other on the translation platform such that the components 402 translate together in unison.

In embodiments, the delivery of light to the optical components 402 may occur through free space or waveguides; however, it may be advantageous in some configurations to employ fiber-based waveguides when optical components 402 undergo translation. A single mode fiber 405 can deliver light from laser source 404 to optical components 402 via fiber coupling 406. One or more optical elements 410 can serve to collimate incoming light from the single mode fiber coupling 406. A single mode or multimode fiber 420 can be used to collect and deliver the light signal to the detector 418. A polarizer 408 and a fiber polarization controller (not shown) can be used to isolate potential polarization effects. Reflector 416 and beam splitter 412 can be arranged in a manner similar to the reflector 114 and splitter 112 in FIG. 2A.

The sample station (e.g., support structure for the sample 116) can have multiple functions, such as, but not limited to, precise environment control, lateral translation, tip-tilt and rolling adjustments. As loading and removing the samples from the mount may affect the angular alignment, tip-tilt adjustment may be useful for addressing any potential misalignment. Transverse and rolling adjustments of the sample may allow for measurements at different spots of the sample. Rolling adjustments (e.g., 180° rolling positions) can be used to offset any potential wedge effects of the sample.

Besides the increased flexibility, use of a single mode fiber may allow for improved spatial filtering, convenient laser wavelength switching and combination, relative ease in adjusting the beam incident angle and angular "bandwidth," and relative ease in scaling the working distance. For surface profiling (e.g., when performing thin film measurements) it may be preferable to compensate for spherical aberration such that the width of the envelope of the SCI signal is narrow. For example, in FIG. 6, a compensator plate 414 having substantially the same apparent thickness as the beam splitter 412 is provided to balance the spherical aberration in both arms of the interferometer.

FIG. 7 shows another configuration of an S-LCI system. Similar to FIG. 6, the optical components 502 are moved with respect to the sample 116, while sample 116 may be relatively fixed. However, beam splitter 412 and compensator plate 414 from FIG. 6 have been replaced with multiple beam splitters. In particular, a pair of cube beam splitters 512 can be used together with beam splitter 514 instead of the flat beam splitter 412. Such a configuration may reduce spherical aberration.

FIG. 8 shows yet another configuration of an S-LCI system. Similar to FIG. 6, the optical components 602 are moved with respect to the sample 116, while sample 116 remains relatively fixed. However, beam splitter 412, compensator plate 414, and reflector 416 from FIG. 6 have been replaced with a single prism 612. Thus, the single prism 612 in FIG. 8 may perform the functions of at least the beam splitter 412 and the reflector 416 in FIG. 6. The prism 612 can be coated or uncoated. In addition to its relative simplicity and compactness, the configuration of FIG. 8 may contain spherical aberration at high incident angle. The shape of the prism can be altered. For example, the bottom surface can be in three different planes for the three beam landings.

Figure 9A:
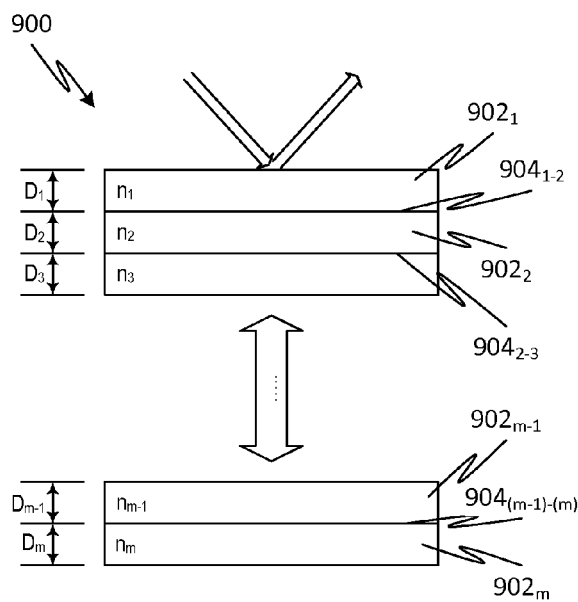
FIG. 9A is a schematic diagram illustrating probing of a multi-layer sample stack, according to one or more embodiments of the disclosed subject matter.

As shown in FIG. 9A, a sample 900 can have multiple layers, for example, m-layers. Each layer 902 can have a respective thickness, D, a respective index of refraction, n, and a boundary 904 separating the layer from an adjacent layer. The top layer $902_1$ and the bottom layer $902_m$ can also have respective external surfaces. An S-LCI system as disclosed herein can be used to interrogate such a sample to produce a plurality of interferogram signals for each layer. Because of the different refractive indices between adjacent layers, the S-LCI signals can be detected at each boundary surface 904 separating the adjacent layers. The refractive index and the thickness can be determined from the phase shift of the interferogram signals. The refractive index information can also be determined from the surface reflectivity which is a function of the incident angle and the state of polarization. As a result, the S-LCI system can be used to map refractive index and size of each layer in a thickness direction of the sample.

Such multi-layer configurations are common in semiconductor devices, optical devices, and thin-film coatings among other areas. The ability to map internal construction of such devices in a non-contact, non-destructive manner would be extremely useful, for example, for quality control, device design and characterization, and process optimization. In addition, with knowledge of the layer composition of the sample, even more precise thickness measurement (e.g., on the order of microns or lower) may be obtainable.

Figure 9B:
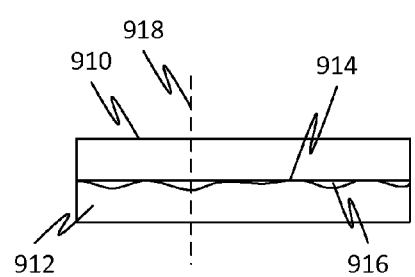
FIG. 9B is a cross-sectional view of a pair of bonded wafers that can be investigated using the disclosed S-LCI systems.

For example, as shown in FIG. 9B, the device may be a pair of bonded semiconductor wafers 910, 912. Imperfect bonding at an interface 914 between the two wafers 910, 912, for example, due to impurities, surface anomalies, or deficiencies in the bonding process, may generate a gap 916. The gap 916 may be an air-filled gap or filled with an impurity, but generally will have a refractive index different than the semiconductor wafers. The S-LCI system can scan in the thickness direction of the bonded wafers, for example, along line 918 to obtain a refractive index/thickness cross-sectional profile that can provide an indication of the existence of bonding defect 916. The S-LCI system may repeat the scans at one or more locations on the device in order to construct a cross-sectional map indicative of the refractive index/thickness variations in the interior of the bonded wafers without having to otherwise cut or destroy the bonded wafers to examine the interior thereof.

Figure 9C:
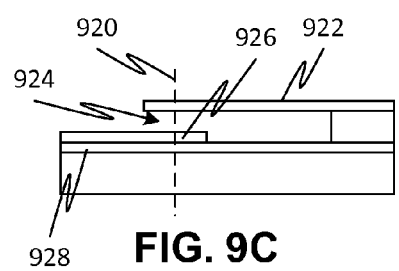
FIG. 9C is a cross-sectional view of a multi-layer MEMS device that can be investigated using the disclosed S-LCI systems.

In another example, as shown in FIG. 9C, the device may be a MEMS device with multiple layers and/or free-standing structures. For example, layer portions of the MEMS device may form micro-structures whose resonant frequency is a function of the thickness and composition of the layers, among other things. The S-LCI system may thus scan the device in the thickness direction thereof along line 920. The resulting interferograms can be used to characterize the refractive index and/or thicknesses of layers 922, 926, and 928, as well as determine the thickness of air gap 924 separating layers 922 and 926. For example, layers 922 and 924 may both be formed of polysilicon while layer 928 may be formed of silicon nitride. As with the example of FIG. 9B, the S-LCI system may repeat the scans at one or more locations on the MEMS device in order to construct a cross-sectional view of the different layers.

The S-LCI system may also be used as feedback during part of the fabrication process. For example, a MEMS device may be periodically interrogated by the S-LCI system during an etching process of a layer of the device to determine the thickness thereof. Timing of the etching process to achieve a desired layer thickness can thus be improved. In addition, because the S-LCI system interrogates the device in a non-contact manner, such interrogation may take place at the same time as the fabrication process, thereby providing real-time feedback without having to halt the fabrication process.

Figure 10:
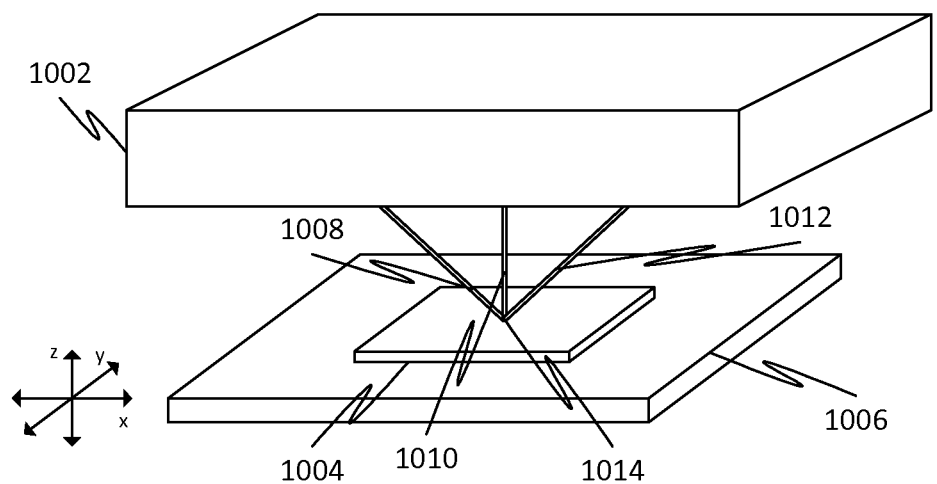
FIG. 10 is a simplified diagram of an S-LCI based metrology device for characterizing a sample, according to one or more embodiments of the disclosed subject matter.
Figure 11:
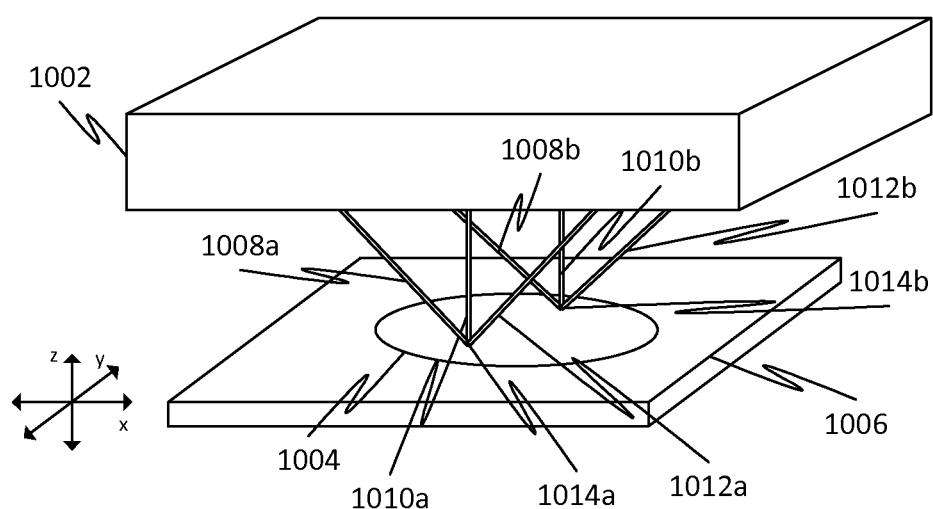
FIG. 11 is a simplified diagram of a multi-probe beam S-LCI based metrology device for characterizing a sample, according to one or more embodiments of the disclosed subject matter.

FIG. 10 shows a metrology instrument for examining a sample, for example, a semiconductor sample, to measure the thickness and/or refractive index of the sample. A sample 1004 can be mounted on a stage 1006 that supports the sample below optical interrogation module 1002. The optical interrogation module 1002 can include the various components for the S-LCI interferometer described above to generate the probe beam 1008 and the on-axis beam 1010. The probe beam 1008 is directed at a specific location 1014 on the sample 1004 to produce reflected beam 1012, which is combined with light in the reference path of the interferometer to produce an interference signal. The interrogation module 1002 can be configured to produce a plurality of probe beams (for example, probe beams 1010a and 1010b in FIG. 11) for simultaneously interrogating two different spots on the sample (for example, spots 1014a and 1014b). Although only two spots are interrogated in FIG. 11, greater than two spots can also be interrogated by providing the appropriate number of optical components.

Figure 12A:
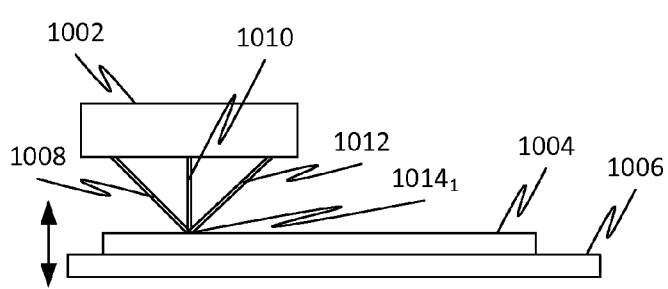
FIGS. 12A-12C are elevation views of an S-LCI based metrology device interrogating multiple locations of a sample, according to one or more embodiments of the disclosed subject matter.
Figure 12D:
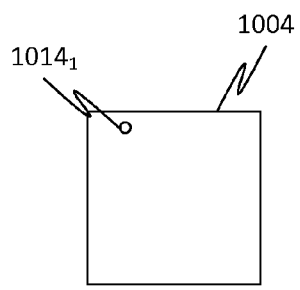
FIG. 12D is a plan view of the interrogation location on the sample surface corresponding to FIG. 12A, according to one or more embodiments of the disclosed subject matter.
Figure 12B:
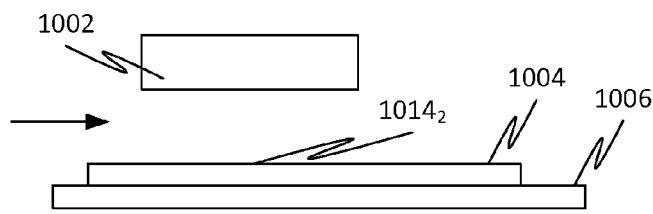
Figure 12C:
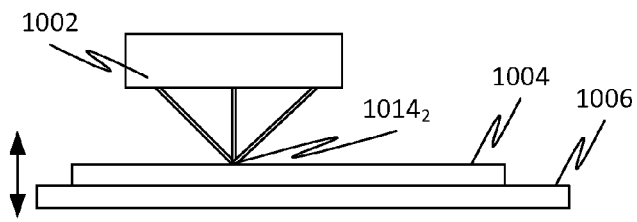
Figure 12E:
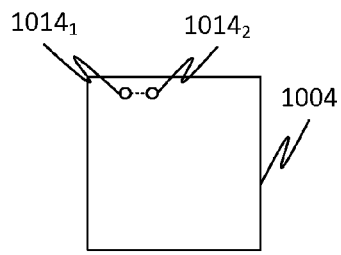
FIG. 12E is a plan view of the interrogation location on the sample surface corresponding to FIG. 12C, according to one or more embodiments of the disclosed subject matter.
Figure 12F:
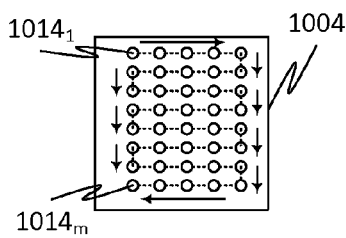
FIG. 12F is a plan view of the interrogation locations on the sample surface after complete evaluation of the sample, according to one or more embodiments of the disclosed subject matter.

Referring to FIGS. 12A and 12D, the interrogation module 1002 can examine a first spot $1014_1$ on a sample 1004. The interrogation module 1002 and/or the stage 1006 can be moved with respect to each other in the z-direction in order to scan the sample in its thickness direction, thereby producing a plurality of interferograms. After acquiring the interferograms, the interrogation module 1002 and/or the stage 1006 can be translated with respect to each other in the x-direction or the y-direction (FIG. 12B) such that a second spot $1014_2$ on the sample 1004 is brought into focus (FIGS. 12C and 12E). The z-direction motion can be performed at the second location $1014_2$ to obtain another plurality of interferograms indicative of the sample properties at the second location $1014_2$. This process may be repeated a plurality of times to interrogate multiple spots 1014 on the sample 1004, for example, as shown in FIG. 12F. Although shown as an array in FIG. 12F, the location of spots $1014i$ is not limited to this configuration. Rather, the location of the spots for interrogation can be chosen based on a number of factors, including, but not limited to, time allotted for a scan, regions of greater interest or sensitivity, and step size and repeatability of translation.

Based on the interferograms, the properties at each location may be mapped to produce a visual indication of property variations across the sample. For example, the thickness of the sample at each spot $1014_i$ can be converted to a type of topographic map showing thickness values or variations across the sample. When the sample is a multi-layer structure, the thickness/refractive index data for each spot can be used to generate a 3-D model of the sample.

Any or both of the interrogation module 1002 and the stage 1006 can be configured to provide the desired motion in three-dimensions. In one example, the interrogation module 1002 moves in the x-, y-, and z-directions while the stage 1006 is fixed. In another example, the interrogation module 1002 moves only in the z-direction while the stage 1006 provides movement in the x- and y-directions. In still another example, one of the interrogation module 1002 and the stage 1006 is capable of motion in the z-direction while the other of the interrogation module and the stage is capable of at least two degrees of motion (e.g., rotation plus translation in a plane a parallel to the x- and y-directions).

Other scanning methodologies for characterizing a sample are also possible according to one or more contemplated embodiments. For example, the S-LCI system may scan in a thickness direction at a first location on the sample until a first interferogram ($S_I$) is detected, after which the S-LCI system may maintain the distance between the sample while proceeding to a second location. At the second location, if the interferogram is not detected, minor scanning in the thickness direction is performed until the interferogram is once again detected. This process may repeat until all desired locations on the sample have been interrogated to generate the first interferogram. The S-LCI system may then return to the first location whereby the process is repeated for the second interferogram ($S_{II}$). The process may be subsequently repeated for any number of additional desired interferograms (e.g., $S_{III}$). Such a technique may be especially useful when the sample is intended to be a homogenous uniform thickness sample. The time required for translation in the thickness direction and thereby the time for the overall characterization of the sample may be minimized or at least reduced.

Figure 13:
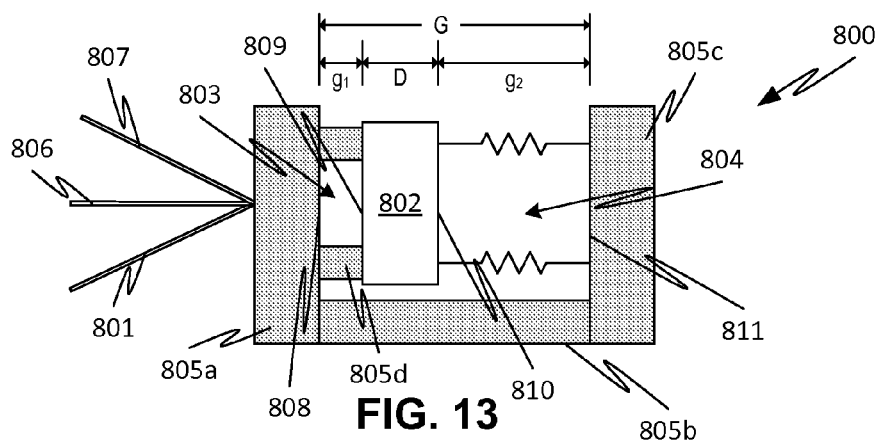
FIG. 13 is a schematic diagram illustrating probing of a sample held by a multi-component glass holder for determining more precisely a thickness of the sample, according to one or more embodiments of the disclosed subject matter.

FIG. 13 shows a transparent sample 802 that is supported in an air cavity in a measurement assembly 800. Probe beam 801 is incident on the assembly with sample 802 contained therein. Reflection from surfaces of the assembly produce reflected beam 807. On-axis beam 806 can be used to monitor displacement of the assembly in the thickness direction thereof (i.e., parallel to the direction of G). Reflection from surface 808, which is adjacent to air cavity 803, may produce the first interferogram signal ($S_I$) at the appropriate translation distance. Reflection from surface 809 of the sample, which is also adjacent to the air cavity 803, may produce the second interferogram signal ($S_{II}$). Similarly, reflections from surface 810 of the sample and from surface 811, which are both adjacent to the air cavity 804, may produce the third interferogram signal ($S_{III}$) and the fourth interferogram signal ($S_{IV}$), respectively. Because the refractive index of air is known, the thickness of the air cavities may be more accurately determined than the sample 802 since it requires no curve fitting.

Determination of the thickness of the air cavities thereby determines the thickness of the sample by simple subtraction. In particular, the geometric thickness, D, of the sample 802 can be indirectly obtained by subtracting the thickness $g_1$ of the air gap 803 and the thickness $g_2$ of the air gap 804 from the overall thickness G. The thickness G can be measured using the S-LCI system prior to insertion of the sample 802 or by other means. A spring or other compression mechanism (not shown) can be used to securely hold the sample within the assembly. For increased stability, the air cavity 806 may be formed as a monolithic assembly of components 805a-d of low constant of thermal expansion (CTE). For example, the components may be formed from fused silica. Joining of components can be made via optical contact bonding for the increased stability, security and erosion resistance.

Alternatively or additionally, the sample or the assembly itself may be formed as a container for holding liquid or gas samples for interrogation. In such an arrangement, the thicknesses of the assembly or the sample container can be determined before addition of the sample by the S-LCI system or by other mechanisms. After addition of the sample gas or liquid to the container/assembly, the S-LCI system can more precisely determine the refractive index of the sample gas or liquid since the thicknesses are already known.

Embodiments of the disclosed subject matter can allows for single-sided interrogation of a sample (i.e., front accessing), such that relatively large size samples or non-transparent samples may be evaluated. In addition, embodiments of the disclosed subject matter have depth-resolving capabilities suitable to accurately measure multi-layer components, such as, but not limited to, microelectromechanical systems (MEMS), microfluidic systems (MFS), semiconductor devices, and multi-layer coatings. In addition, the depth resolving capabilities of embodiments of the disclosed subject matter may be used to probe or characterize depth and/or properties of fabrication artifacts, for example, a wafer-bonding internal interface. Moreover, a dual-axis low numerical aperture (NA) system according to one or more embodiments of the disclosed subject matter can offer longer working distances at a lower cost than single axis higher numerical aperture systems.

Although a substantially monochromatic light source has been discussed above, it is also appreciated that the light source can include multiple discrete wavelengths according to one or more embodiments of the disclosed subject matter. For example, the light source can be a single laser with multiple longitudinal modes, such as with laser combs, or a combination of multiple lasers. In another example, the light can be single or multiple emission lines from a lamp. It can be relatively straightforward to implement multiple wavelengths such that test results are produced at different wavelengths. In such cases, the beams of different wavelengths can be spatially overlapped such that the geometric thickness measurement is substantially the same. This additional information can help to improve the measurement accuracy at each individual wavelength. Because of the spatial low coherence, the signal of each wavelength component has an expansion in the Fourier domain. The wavelength separation can be large enough to avoid, or at least reduce, signal overlap in the Fourier domain.

The state of polarization can be programmable by rotating one or more polarizers in the beam path. The S-LCI system scans can be carried out at different discrete or continuous polarization rotations. Embodiments of the disclosed S-LCI system can thus combine features of the S-LCI system function discussed above with that of an ellipsometer. Surface reflections and refractions can also be used for polarization manipulation. Moreover, an instrument can be constructed which combines S-LCI system functionality with T-LCI system functionality by sharing common scanning and signal acquisition.

It will be appreciated that the modules, processes, systems, and sections described above can be implemented in hardware, hardware programmed by software, software instruction stored on a non-transitory computer readable medium or a combination of the above. A system for measuring refractive index and thickness using an interferometer can be implemented, for example, using a processor configured to execute a sequence of programmed instructions stored on a non-transitory computer readable medium. The processor can include, but is not limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, or another structured or object-oriented programming language. The sequence of programmed instructions and data associated therewith can be stored in a non-transitory computer-readable medium such as a computer memory or storage device which can be any suitable memory apparatus, such as, but not limited to read-only memory (ROM), programmable read-only memory (PROM), electrically erasable programmable read-only memory (EEPROM), random-access memory (RAM), flash memory, disk drive, etc.

Furthermore, the modules, processes, systems, and sections can be implemented as a single processor or as a distributed processor. Further, it should be appreciated that the steps discussed herein can be performed on a single or distributed processor (single and/or multi-core). Also, the processes, modules, and sub-modules described in the various figures of and for embodiments above can be distributed across multiple computers or systems or can be co-located in a single processor or system. Exemplary structural embodiment alternatives suitable for implementing the modules, sections, systems, means, or processes described herein are provided below, but not limited thereto. The modules, processors or systems described herein can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example. Moreover, embodiments of the disclosed method, system, and computer program product can be implemented in software executed on a programmed general purpose computer, a special purpose computer, a microprocessor, or the like.

Embodiments of the method and system (or their sub-components or modules), can be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, etc. In general, any process capable of implementing the functions or steps described herein can be used to implement embodiments of the method, system, or a computer program product (software program stored on a non-transitory computer readable medium).

Furthermore, embodiments of the disclosed method, system, and computer program product can be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the functional descriptions provided herein and with a general basic knowledge of optics, interferometry, and/or computer programming arts.

Features of the disclosed embodiments can be combined, rearranged, omitted, etc., within the scope of the invention to produce additional embodiments. Furthermore, certain features can sometimes be used to advantage without a corresponding use of other features.

It is thus apparent that there is provided in accordance with the present disclosure, system, methods, and devices for measurement of refractive index and thickness using low-coherence interferometers. Many alternatives, modifications, and variations are enabled by the present disclosure. While specific embodiments have been shown and described in detail to illustrate the application of the principles of the present invention, it will be understood that the invention can be embodied otherwise without departing from such principles. Accordingly, Applicants intend to embrace all such alternatives, modifications, equivalents, and variations that are within the spirit and scope of the present invention.

The invention claimed is:

1. A method of determining thickness and refractive index of a sample, the method comprising:
 directing a first beam of substantially monochromatic light from a low coherence laser source onto a beam splitter at an angle so as to direct respective components of the first beam along a first optical path and along a second optical path, light components directed along the first optical path being incident on a reflector, light components directed along the second optical path being incident on the sample, the reflector being located on an opposite side of the beam splitter from the sample;
 simultaneously with said directing, further directing a collimated beam from the monochromatic light along an optical axis extending from the reflector to the sample;
 detecting light along the optical axis reflected from the sample so as to generate an on-axis interference signal;
 determining changes in the distance between the sample and the beam splitter on the basis of the on-axis interference signal;
 combining light components from the first optical path reflected by the reflector with light components from the second optical path reflected by the sample so as to generate an interference pattern;
 changing a distance between the sample and the beam splitter;
 repeating the directing and the combining to generate another interference pattern; and
 simultaneously determining the thickness and refractive index of at least a portion of the sample on the basis of the generated interference patterns.

2. The method of claim 1, wherein said first beam is one of a converging beam of light, a diverging beam of light, or an uncollimated beam of light.

3. The method of claim 1, wherein during said changing the distance, a distance between the beam splitter and the reflector is maintained.

4. The method of claim 1, wherein said angle is approximately 30°.

5. The method of claim 1, wherein said changing the distance includes translating the sample toward or away from the reflector.

6. The method of claim 1, wherein said changing the distance includes translating the beam splitter and the reflector toward or away from the sample.

7. The method of claim 1, wherein said sample includes a gas or fluid.

8. The method of claim 1, wherein said sample includes a parallel plane glass plate.

9. The method of claim 1, wherein said sample includes a multi-layer substrate.

10. The method of claim 1, wherein said sample includes a semiconductor wafer.

11. A system for determining thickness and refractive index information for a sample, the system comprising:
 a substantially monochromatic low coherence laser source;
 an interferometer forming two beam paths, the sample being arranged with respect to one of the beam paths;

first optical components constructed and arranged to generate a first light beam from an output of the light source, the first light beam being directed at an angle with respect to an axis of the interferometer, the axis being normal to a surface of the sample;

second optical components constructed and arranged to generate a collimated light beam from the output of the light source, the collimated light beam being directed to the interferometer along said axis;

a first detector arranged to detect light output from the interferometer at an angle with respect to the interferometer axis;

a second detector aligned with the interferometer axis to detect light reflected along said axis;

a scanning mechanism configured to move one of the sample and the interferometer with respect to the other in a direction parallel to the interferometer axis; and a processor configured to use signals from the first and second detectors to simultaneously determine thickness and refractive index information for at least a portion of the sample using the following equations:

$$\frac{4\pi}{\lambda} n_2 t_2 * \cos k =$$
$$\phi_\square^{S_I}(d_1, \cos j) - \phi_\square^{S_{II}}(d_{11}, \cos j) + (\phi_\square^{ref}(d_n) - \phi_\square^{ref}(d_1)) * \cos j \pm \pi,$$

and $$n_2 \sin k = n_{air} \sin j,$$

where:
j represents an incident angle in the air and k represents an incident angle in the sample, $\lambda$ is the wavelength of the laser source in vacuum; $n_2$ represents the refractive index of the sample; $t_2$ represents the thickness of the sample, $d_I$ represents an arbitrarily chosen air thickness value near the center region of the interferogram signal $S_I$, and $d_{II}$ represents an arbitrarily chosen air thickness value near the center region of the interferogram signal $S_{II}$, $\phi_\square^{S_I}$ represents a phase shift of the first sample location signal, $\phi_\square^{S_{II}}$ represents a phase shift of the second sample location signal and $\phi_\square^{ref}$ represents a phase shift of the on-axis signal.

12. The system of claim 11, wherein the first optical components are constructed and arranged to generate the first light beam as a converging light beam.

13. The system of claim 11, wherein the interferometer includes one or more beam splitters and one or more fixed reflectors arranged to form the two beam paths.

14. The system of claim 11, wherein the interferometer includes at least one of a beam splitter, a compensator, and a prism arranged to form the two beam paths.

15. The system of claim 11, wherein the first optical components include a polarizer constructed and arranged to generate the first light beam.

16. The system of claim 11, further comprising a single mode fiber between the light source and the first optical components, and a multi-mode fiber between the second optical components and the second detector.

17. A sample measurement method comprising:
directing a first portion of substantially monochromatic light to a first arm of an interferometer, the first arm including a reflection surface arranged at a first distance along an input beam path of the first arm and reflecting light incident thereon from said first arm input path to an output beam path;

directing a second portion of the substantially monochromatic light to a second arm of the interferometer, the second arm including a sample arranged along the input beam path of the second arm, internal boundaries or external surfaces of the sample reflecting light incident thereon from said second arm input path to the output beam path;

translating the sample while directing the first and second portions of the light, an interference pattern being formed by the combination of light in the output beam path when one of said internal boundaries or external surfaces of the sample is at a distance along the second arm input beam path approximately equal to the first distance along the first arm input beam path;

detecting the combination of light and generating signals indicative of a plurality of the interference patterns formed during the translating;

simultaneously calculating at least a refractive index and a thickness of the sample based on said signals;

directing a third portion of the substantially monochromatic light in a direction perpendicular to a top surface of the sample and on the top surface at a location where the second portion is incident on the sample, the top surface reflecting light incident thereon;

detecting the reflected third portion from the top surface during the translating to produce an on-axis interference signal; and calculating displacement of the sample during the translating based on said on-axis interference signal.

18. The method of claim 17, wherein the calculating includes determining locations of the internal boundaries in a thickness direction of the sample.

19. The method of claim 17, wherein the internal boundaries are boundaries between regions of different refractive indices in the sample.

20. The method of claim 17, wherein the calculating includes performing a Fourier transform on said signals to generate Fourier phase signals, and calculating refractive index and thickness based on the phase signals.

21. The method of claim 17, wherein the sample is not rotated during the translating that generates the plurality of the interference patterns.

22. The method of claim 17, further comprising, moving the sample in a direction perpendicular to the thickness direction to a new location, and subsequently repeating the directing, translating, detecting, and calculation for the new sample location.

23. The method of claim 17, wherein a first interference pattern is produced by reflection of the second portion from a top surface of the sample, a second interference pattern is produced by reflection of the second portion from a bottom surface of the sample, and a third interference pattern is produced by multiple internal reflections within the sample.

24. A system for measuring a sample, the system comprising:
a low coherence laser source that produces a narrow band of light at a substantially single wavelength;

an interferometer having a reference beam path, a sample beam path, and a beam splitter, the beam splitter dividing light input to the interferometer and directing first and second portions of the light to the reference beam path and the sample beam path, respectively, the first portion of the light being incident on a reference reflector in the reference beam path, the second portion of the light being incident on the sample in the sample beam path at an angle with respect to a thickness direction of the sample, the light reflected by both the reference reflector and the sample being combined as an output of the interferometer;

a translation device configured to translate one of the interferometer and the sample with respect to the other in a thickness direction of the sample;

a detection device configured to detect the interferometer output and generates interferogram signals based thereon; and a controller coupled to the detector and configured to simultaneously determine refractive index and geometric thickness of at least a portion of the sample based on the generated interferogram signals, wherein the controller is configured to:

perform a Fourier transform on at least two of the interferogram signals so as to generate Fourier phase data;

calculate phase delay caused by the sample based on the phase data from the at least two of the interferogram signals, and calculate the refractive index and the thickness of the at least a portion of the sample based on the calculated phase delay using the following equations:

$$\frac{4\pi}{\lambda} n_2 t_2 * \cos k = \phi_\Box^{S_I}(d_1, \cos j) - \phi_\Box^{S_{II}}(d_{11}, \cos j) + (\phi_\Box^{ref}(d_n) - \phi_\Box^{ref}(d_1)) * \cos j \pm \pi,$$

and $$n_2 \sin k = n_{air} \sin j,$$

where:

j represents an incident angle in the air and k represent an incident angle in the sample, $\lambda$ is the wavelength of the laser in vacuum; $n_2$ represents the refractive index of the sample; $t_2$ represents the thickness of the sample, $d_I$ represents an arbitrarily chosen air thickness value near the center region of the interferogram signal $S_I$, and $d_{II}$ represents an arbitrarily chosen air thickness value near the center region of the interferogram signal $S_{II}$, $\phi_\Box^{S_I}$ represents a phase shift of the first sample location signal, $\phi_\Box^{S_{II}}$ represents a phase shift of the second sample location signal and $\phi^{ref}$ represents a phase shift of the on-axis signal.

25. The system of claim 24, wherein the controller is configured to calculate the refractive index and thickness based on the calculated phase delay by performing a least-squares fit.

26. The system of claim 24, further comprising a sample tracking module configured to measure displacement of the sample by the translation device in the thickness direction.

27. The system of claim 26, wherein the sample tracking module is constructed to measure displacement of the sample using an interference signal produced using light from the light source directed substantially perpendicular to a top surface of the sample.

28. A system for measuring a sample, the system comprising:

a spatial low-coherence interferometer having a monochromatic light input and outputting combined light reflected by a sample in a sample path and by a reference mirror in a reference path;

a translation device for moving one of the sample or the interferometer with respect to the other in a thickness direction of the sample; and a controller configured to simultaneously calculate refractive index and thickness of the sample based on interferograms detected in light output from the interferometer with the sample at different locations in the thickness direction using the following equations:

$$\frac{4\pi}{\lambda} n_2 t_2 * \cos k = \phi_\Box^{S_I}(d_I, \cos j) - \phi_\Box^{S_{II}}(d_{II}, \cos j) + (\phi_\Box^{ref}(d_{II}) - \phi_\Box^{ref}(d_I)) * \cos j \pm \pi,$$

and $$n_2 \sin k = n_{air} \sin j,$$

where:

j represents an incident angle in the air and k represent an incident angle in the sample, $\lambda$ is the wavelength of a laser beam in vacuum; $n_2$ represents the refractive index of the sample; $t_2$ represents the thickness of the sample, $d_I$ represents an arbitrarily chosen air thickness value near the center region of the interferogram signal $S_I$, and $d_{II}$ represents an arbitrarily chosen air thickness value near the center region of the interferogram signal $S_{II}$, $\phi_\Box^{S_I}$ represents a phase shift of the first sample location signal, $\phi_\Box^{S_{II}}$ represents a phase shift of the second sample location signal and $\phi^{ref}$ represents a phase shift of the on-axis signal.

29. The system of claim 28, wherein the controller performs a Fourier transform to extract phase delay data from at least two of the interferograms and performs a least squares fit to calculate refractive index and thickness of the sample based on said phase delay data.

* * * * *